United States Patent [19]

Markiewitz et al.

[11] 4,195,146

[45] Mar. 25, 1980

[54] ESTERS OF CARBOXY AMINO PHENYL ISOCYANURATES AND VINYLIDENE CARBONYL OXY ALKANOLS

[75] Inventors: Kenneth H. Markiewitz; Alfred J. Restaino, both of Wilmington, Del.

[73] Assignee: ICI Americas Inc., Wilmington, Del.

[21] Appl. No.: 923,265

[22] Filed: Jul. 10, 1978

Related U.S. Application Data

[63] Continuation-in-part of Ser. No. 819,353, Jul. 27, 1977, abandoned.

[51] Int. Cl.$^2$ ............................................. C08G 18/67
[52] U.S. Cl. ..................................... 526/261; 252/182; 252/188.3 R; 528/49; 528/73; 528/75
[58] Field of Search ........................... 528/49, 73, 75; 526/261; 252/182, 188.3

[56] References Cited

U.S. PATENT DOCUMENTS

| | | | |
|---|---|---|---|
| 2,947,736 | 8/1960 | Lundberg | 526/261 |
| 2,952,665 | 9/1960 | Bunge et al. | 260/77.5 NC |
| 2,958,704 | 11/1960 | Dinbergs et al. | 260/468 |
| 2,993,870 | 7/1961 | Burkus | 521/116 |
| 3,037,979 | 6/1962 | Fukui et al. | 526/261 |
| 3,041,313 | 6/1962 | Lavin et al. | 260/67 |
| 3,061,591 | 10/1962 | Roth | 260/77.5 NC |
| 3,065,231 | 11/1962 | Frazier et al. | 260/77.5 NC |
| 3,154,522 | 10/1964 | Beitchman | 260/77.5 NC |
| 3,168,483 | 2/1965 | Beitchman et al. | 252/426 |
| 3,251,818 | 5/1966 | Juenge et al. | 526/261 |
| 3,252,942 | 5/1966 | France et al. | 260/77.5 NC |
| 3,297,745 | 1/1967 | Fekete et al. | 260/471 |
| 3,332,946 | 7/1967 | Little | 526/261 |
| 3,376,301 | 4/1968 | Francis et al. | 526/261 |
| 3,437,500 | 4/1969 | Hennig et al. | 106/252 |
| 3,522,253 | 7/1970 | Little et al. | 526/261 |
| 3,609,149 | 9/1971 | Matsui et al. | 260/77.5 NC |
| 3,642,943 | 2/1972 | Noel | 260/859 R |
| 3,658,801 | 4/1972 | Berry et al. | 526/261 |
| 3,658,801 | 4/1972 | Berry et al. | 260/77.5 NC |
| 3,694,415 | 9/1972 | Honda et al. | 260/77.5 CR |
| 3,719,638 | 3/1973 | Huemmer et al. | 260/77.5 CR |
| 3,723,367 | 3/1973 | Chow et al. | 260/2.5 AB |
| 3,763,269 | 10/1973 | Formaini | 260/75 UA |
| 3,786,030 | 1/1974 | Rice | 260/77.5 NC |
| 3,821,067 | 6/1974 | Taylor et al. | 260/37 N |
| 3,821,098 | 6/1974 | Garratt et al. | 204/159.22 |
| 3,840,618 | 10/1974 | Da Fano | 260/863 |
| 3,849,349 | 11/1974 | Frisch | 260/2.5 AW |
| 3,850,770 | 11/1974 | Juna et al. | 204/159.19 |
| 3,852,220 | 12/1974 | Kimmel et al. | 252/524 |
| 3,860,673 | 1/1975 | Lawrence | 260/859 R |
| 3,872,035 | 3/1975 | Papa et al. | 260/2.5 AW |
| 3,876,728 | 4/1975 | Kuroda et al. | 260/859 R |
| 3,884,917 | 5/1975 | Ibbotson | 260/77.5 NC |
| 3,914,335 | 10/1975 | Tugukuni et al. | 260/859 R |
| 3,925,335 | 12/1975 | Kuehn | 260/859 R |
| 3,926,875 | 12/1975 | Tsugukuni et al. | 260/23 TN |
| 3,932,401 | 1/1976 | Berg et al. | 96/115 P |
| 3,943,075 | 3/1976 | Fishbein et al. | 260/2.5 AW |

FOREIGN PATENT DOCUMENTS

| | | | |
|---|---|---|---|
| 816888 | 6/1974 | Belgium | 260/77.5 NC |
| 1495558 | 8/1967 | France . | |
| 2283916 | 4/1976 | France . | |
| 629015 | 9/1949 | United Kingdom | 260/77.5 CR |
| 809809 | 3/1959 | United Kingdom | 260/77.5 NC |

OTHER PUBLICATIONS

Muller, *Methoden der Organischen Chemie*, (Houben-Weyl), vol. VIII, 1952, pp. 141 & 142.

*Primary Examiner*—Maurice J. Welsh

[57] ABSTRACT

Disclosed are unsaturated isocyanurates of monourethanes of an aromatic polyisocyanate and a vinylidene carbonyl oxy alkanol characterized by one of the following formulae:

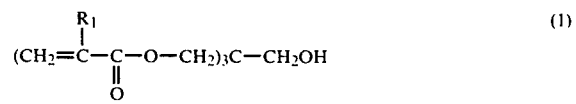

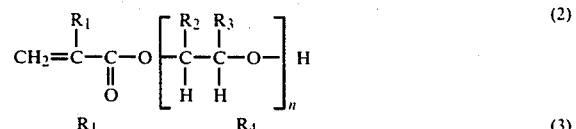

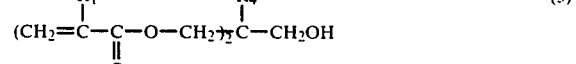

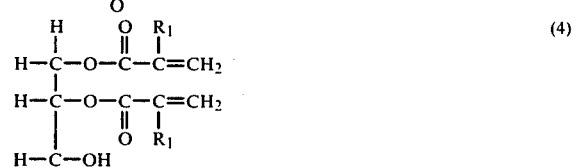

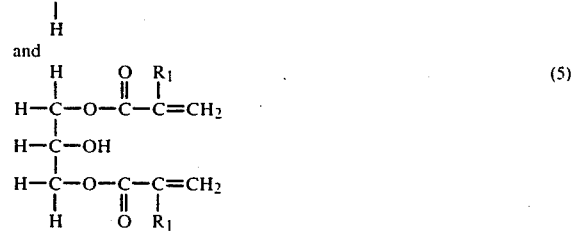

wherein $R_1$ is hydrogen or an alkyl group containing from one to four carbon atoms, $R_2$ is hydrogen, alkyl containing from 1 to 12 carbon atoms, or a chlorinated, brominated, or fluorinated alkyl group containing from 1 to 12 carbon atoms, $R_3$ is hydrogen, alkyl containing from 1 to 12 carbon atoms, or a chlorinated, brominated, or fluorinated alkyl group containing from 1 to 12 carbon atoms, $R_4$ is hydrogen, methyl or ethyl, and n is from one to four, with the proviso that $R_2$ and $R_3$ on adjacent carbon atoms are not both alkyl or chlorinated, brominated, or fluorinated alkyl. The unsaturated isocyanurates may be homopolymerized or copolymerized with ethylenically unsaturated compounds to form isocyanurate polymers having excellent physical properties at high temperatures.

34 Claims, No Drawings

ESTERS OF CARBOXY AMINO PHENYL ISOCYANURATES AND VINYLIDENE CARBONYL OXY ALKANOLS

This application is a continuation-in-part of application Ser. No. 819,353 filed July 27, 1977, now abandoned.

BACKGROUND OF THE INVENTION

The present invention relates to isocyanurates, and to compositions useful in the preparation of polymeric isocyanurates. More particularly, the present invention relates to isocyanurates which when cured have excellent physical properties at high temperatures.

The expression "vinylidene group" when used in this application means the group characterized by the formula:

wherein the two free valence bonds are not both connected to the same carbon atom.

The expression "aromatic polyisocyanate" when used in this application means a compound containing at least 2 isocyanate groups attached directly to the carbon atom of an aromatic ring.

The expression "isocyanurate" means a compound containing the structure:

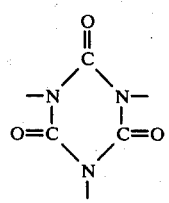

The products of this invention may be generally classified as thermoset resins. The prior art thermoset resins lack one or more important physical properties which would be desirable in their use. It is an object of this invention to prepare curable thermosetting compositions which combine excellent viscosity control at low as well as high dissolved solids concentrations; which are easily handled for laminate preparation; which may be blended with copper salts to yield a low exotherm on cure to prevent bubbling and warpage; which have a broad range of solubility in vinylidene monomers with which it is copolymerizable; which when cured form thermoset resins which exhibit good corrosion resistance in a variety of media, including water, acid and alkali; and which yield cured resins with superior stiffness and rigidity and excellent retention of physical properties at elevated temperatures.

It has been discovered that all of these properties are now achievable with the products of this invention and that it is also possible to combine these desirable properties with fire retardance and low smoke. The versatility of these resin systems makes possible the preparation of a wide range of products with properties superior to general purpose polyester resins and isophthalic resins, as well as other specialty vinyl ester resins.

The resins of this invention are further characterized by a very high level of aromatic and cyclic character which are derived both from the aromatic polyisocyanate and from the isocyanurate ring. This high degree of aromatic and cyclic character is believed by contribute substantially to the improved thermal stability and to the stiffness and rigidity of the products prepared therefrom. The combination of these highly aromatic and cyclic compositions with acrylate and methacrylate unsaturation makes possible a rapid curing system with excellent retention of physical properties not readily achievable from prior art products. It also allows for a versatile solubility in a variety of comonomers with which the products of this invention will copolymerize. The products of this invention have a molecular weight range that allows the proper solution viscosity (about 100 to about 1000 cps) for good handling and lay-up when making laminates. Products of this invention have a viscosity above 1000 cps may also be prepared for use in applications requiring high viscosity. The products of this invention can be prepared at low solids concentration and still exhibit the proper viscosity for good handling.

The isocyanurates of this invention are isocyanurates of urethanes of an aromatic polyisocyanate and at least one vinylidene carbonyl oxy alkanol characterized by one of the following formulae:

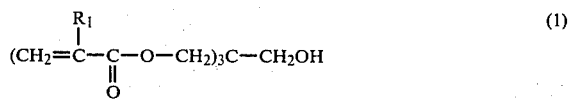 (1)

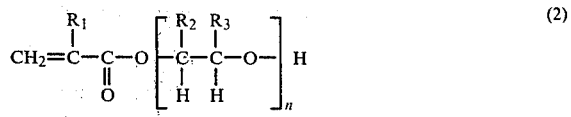 (2)

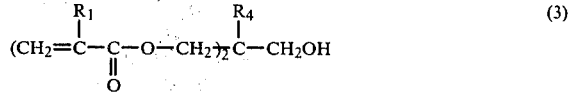 (3)

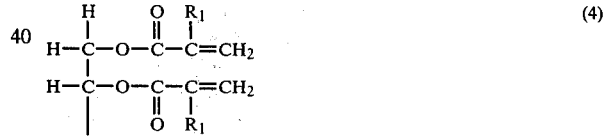 (4)

and

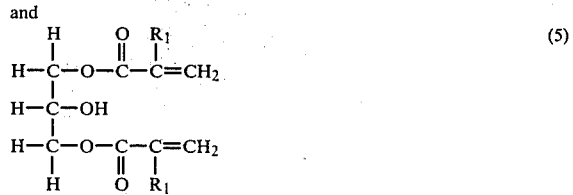 (5)

wherein $R_1$ is hydrogen or an alkyl group containing from 1 to 4 carbon atoms, $R_2$ is hydrogen, alkyl containing from 1 to 12 carbon atoms, or a chlorinated, brominated, or fluorinated alkyl group containing from 1 to 12 carbon atoms, $R_3$ is hydrogen, alkyl containing from 1 to 12 carbon atoms, or a chlorinated, brominated, or fluorinated alkyl group containing from 1 to 12 carbon atoms, $R_4$ is hydrogen, methyl or ethyl, and n is from one to four, with the proviso that $R_2$ and $R_3$ on adjacent carbon atoms are not both alkyl or chlorinated, brominated, or fluorinated alkyl, that is at least one of $R_2$ and $R_3$ must be hydrogen. In order to obtain resins having the excellent combination of high temperature physical properties provided by the present invention, it is essential that the resin be prepared from an unsaturated isocyanurate composition wherein at least a major amount of the isocyanurate moieties are based on one or more vinylidene carbonyl oxy alkanols defined above. Illustrative examples of such alkanols include; hydroxypropyl methacrylate, hydroxyethyl methacrylate, hydroxypropyl acrylate, hydroxyethyl acrylate, pentaerythritol triacylate, pentaerythritol trimethacrylate, and diacrylates and dimethacrylates of trimethol propane, trimethylol ethane, trimethylol methane, and glycerol. A preferred group of vinylidene carbonyl oxy alkanols include hydroxypropyl methacrylate, hydroxyethyl methacrylate, hydroxypropyl acrylate, hydroxyethgyl acrylate, and blends thereof. Another preferred group of such alkanols are blends of polyfunctional acrylates or methacrylates such as pentaerythritol triacrylate, pentaerythritol trimethacrylate, and mixtures thereof, with one or more monofunctional acrylates or methacrylates such as hydroxypropyl acrylate, hydroxypropyl methacrylate, hydroxyethyl acrylate, and hydroxyethyl methacrylate.

While the isocyanurates of this invention must contain moieties derived from one of the vinylidene carbonyl oxy alkanols defined above, the moieties derived from an aromatic polyisocyanate may be based on any trimerizable aromatic polyisocyanate. In fact, any trimerizable aromatic polyisocyanate which is conventionally used in the art for the preparation of isocyanurates may be used to prepare the isocyanurate compositions of the present invention. For example, the aromatic polyisocyanate may or may not contain ethylenic unsaturation and it may be monomeric or polymeric. The only requirements are that the aromatic polyisocyanate contain at least two aromatic isocyanate groups, be trimerizable, and be free of any groups which interfere with the trimerization of isocyanate groups or which interfere in the reaction of an isocyanate group with a hydroxyl group. Illustrative examples of aromatic polyisocyanates which are particularly useful in the preparation of isocyanurate compositions of this invention include: 2,4-tolylene diisocyanate; 2,6-tolylene diisocyanate; m-phenylene diisocyanate; p-phenylene diisocyanate; 1,5-naphthalene diisocyanate; 4,4'-diphenyl ether diisocyanate; 4,4',4''-triphenylmethane triisocyanate; 2,4,4'-triisocyanatodiphenylmethane; 2,2',4-triisocyanato diphenyl; 4,4'-diphenylmethane diisocyanate; 4,4'-benzophenone diisocyanate; 2,2-bis(4-isocyanatophenyl)propane; 1,4-naphthalene diisocyanate; 4-methoxy-1,3-phenylene diisocyanate; 4-chloro-1,3-phenylenediisocyanate; 4-bromo-1,3-phenylene diisocyanate; 4-ethoxy-1,3-phenylene diisocyanate; 2,4'-diisocyanatodiphenyl ether; 4,4'-diisocyanatodiphenyl; 9,10-anthracene diisocyanate; 4,6-dimethyl-1,3-phenylene diisocyanate; 4,4'-diisocyanatodibenzyl; 3,3'-dimethyl-4,4'-diisocyanatodiphenylmethane; 3,3'-dimethyl-4,4'-diisocyanatodiphenyl; 3,3'-dimethoxy-4,4'-diisocyanatodiphenyl; 1,8-naphthalene diisocyanate; 2,4,6-tolylene triisocyanate; 2,4,4'-triisocyanatodiphenyl ether, diphenylmethane diisocyanate, polymethylene polyphenylene polyisocyanate available under the trademarks Mondur and Papi, having a functionality of 2.1 to 2.7; 1,3-xylene 4,6-diisocyanate; aromatic isocyanate terminated polyurethanes; and aromatic isocyanate terminated pre-polymers of polyesters. Although it is preferred to use all aromatic polyisocyanate, small amounts of an aliphatic polyisocyanate, for example, 1,6-hexamethylene diisocyanate, isophorone diisocyanate, or alpha,alpha'-diisocyanato-p-xylene, may be used in combination with the aromatic polyisocyanate.

Small amounts of monoisocyanates may be present to modify the structure of the isocyanurate formed. The use of small amounts of monoisocyanates improves elongation and gives better control of the reaction to prevent gelation, particularly when triisocyanates are used. The amount of monisocyanate used is usually selected to furnish a ratio of isocyanate groups originating with monoisocyanates to isocyanate groups originating with polyisocyanate of not more than 0.5, and preferably a ratio of not more than about 0.3. Typical examples of monoisocyanates which may be used include p-tolylisocyanate, phenylisocyanate, and n-butylisocyanate. Preferred polyisocyanates are 2,4-tolylene diisocyanate, 2,6-tolylene diisocyanate, 4,4'-diphenylmethane diisocyanate, polymethylene polyphenylene polyisocyanates having an average functionality of 2.1 to 2.7, and mixtures thereof.

The unsaturated isocyanurate compositions of this invention are a mixture of urethane containing unsaturated isocyanurates of an aromatic polyisocyanate and at least one vinylidene carbonyl oxy alkanol characterized by one of the above formulae. The exact structure of each component of these compositions and the precise amount of each component present in the compositions are not known. However, it is known that the essential components of the isocyanurate compositions of this invention contain vinyl groups, ester groups, urethane groups and isocyanurate groups. It is also believed that these groups are linked together in the following sequence: vinylester-urethane-isocyanate ring. Although applicants do not wish to be bound to a particular structural formula, it is believed that preferred unsaturated isocyanurate compositions of this invention are a mixture of isocyanurates characterized by the following formulae:

wherein R'' is an aromatic radical free of a group which is reactive with an isocyanate group and is obtained by removing the isocyanate groups from an aromatic polyisocyanate, wherein x is an integer which is one less than the number of isocyanate groups present in the polyisocyanate, wherein each R' is independently

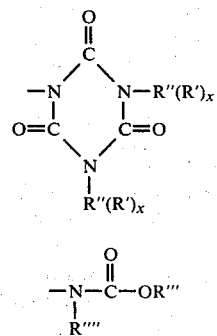

with the proviso that at least one R' is

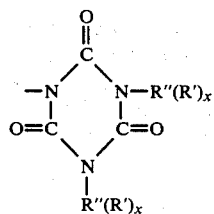

and with the proviso that each terminal R' is

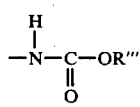

wherein R''' is a monovalent organic radical having the formula obtained by removing a hydroxyl group from a vinylidene carbonyl oxy alkanol characterized by formulae (1) thru (5) recited above and where each R'''' is independently—H or

and wherein the total number of isocyanurate rings in each molecule is less than about 400.

It is apparent from the foregoing formula that the isocyanurates of this invention may also be described as esters of carboxy amino phenyl isocyanurates and vinylidene carbonyl oxy alkanols. These esters contain one or more isocyanurate ring per molecule or, as is usually the case, comprise a mixture of ester containing one isocyanurate ring per molecule with ester containing more than one isocyanurate ring per molecule. These esters may or may not contain allophanate groups. Prior to curing, the solid isocyanurates of this invention are fusible, that is, they exhibit a softening point by the Ring and Ball method described in the A.S.T.M. Designation E28-58T.

Preferred isocyanurate compositions of this invention exhibit characteristic infra-red (IR) peaks at 5.75–6 microns (carbonyl), 6.1–6.35 microns (amidic hydrogen), 6.9–7.2 microns (isocyanurate), and 10.15–10.85 microns (vinyl). A preferred class of isocyanurates have IR peaks at 5.8–5.95 microns, 6.2–6.3 microns, 7.00–7.15 microns, and 10.2–10.75 microns. Preferred isocyanurates of this invention which are prepared with toluene diisocyanate and hydroxylpropyl methacrylate exhibit IR peaks in styrene at about 5.85 microns, about 6.23 microns, about 7.1 microns, and about 10.6 microns.

The isocyanurate compositions of this invention which are styrene solutions of isocyanurates based on toluene diisocyanate and hydroxylpropyl methacrylate may be further characterized within experimental error by the following nuclear magnetic resonance (NMR) signals at: 9.6±0.2, 8.8±0.2, 7.50, 7.48, 7.44, 7.41, 7.36, 7.33, 7.29, 7.26, 6.79, 6.71, 6.57, 5.93, 5.91, 5.70, 5.69, 5.33, 5.31, and 5.19. The isocyanurate compositions of this invention which contain allophanate groups will give an additional NMR signal at 10.6±0.2. All NMR measurements recited in this application were determined by proton magnetic resonance spectral measurements on a Varian CFT-20 spectrometer operating at 79.54 MHz (nominal 80 MHz) at 30° C. Dimethyl sulfoxide was used as solvent. The results are quoted as chemical shifts in parts per million (ppm) relative to tetramethyl silane as internal standard.

The unsaturated isocyanurate compositions of this invention are all soluble in at least one of the following free-radical polymerizable ethylenically unsaturated monomers: divinylbenzene, styrene, methyl acrylate, methyl methacrylate, ethyl acrylate, ethyl methacrylate, 2-ethylhexyl acrylate, 2-ethylhexyl methacrylate, butyl acrylate, butyl methacrylate, tetramethylene glycol diacrylate, trimethylol propane triacrylate, pentaerythritol triacrylate, neopentyl glycol diacrylate, 1,3-butylene glycol diacrylate, 2,3-dibromopropyl acrylate, 2,3-dibromopropyl methacrylate, cyclohexyl acrylate, cyclohexyl methacrylate, acrylic acid, methacrylic acid, hydroxyethyl acrylate, hydroxyethyl methacrylate, hydroxypropyl acrylate, hydroxypropyl methacrylate, chlorostyrene, acrylonitrile, vinylidene chloride, vinyl acetate, vinyl stearate, vinyltolylene, hexanediol diacrylate, hexanediol dimethacrylate, and mixtures thereof. The term "soluble" means that at least two grams of the isocyanurate composition can be dissolved in 100 grams of at least one of the above-listed ethylenically unsaturated monomers at 25° C.

The ethylenically unsaturated isocyanurate compositions of this invention may be prepared by reacting an aromatic polyisocyanate with one of the above-described vinylidene carbonyl oxy alkanols to form an isocyanate containing urethane and then trimerizing the isocyanate-containing urethane until essentially all isocyanate groups have reacted to form the ethylenically unsaturated isocyanurate composition of this invention. It will be understood, of course, that the resulting isocyanate composition may contain some residual isocyanate groups. Other methods of preparing the isocyanurates will be apparent to those skilled in this art.

More particularly, the isocyanurate compositions of this invention may be prepared by the method described in patent application Ser. No. 819,353, entitled "ESTERS OF CARBOXY AMINO PHENYL ISOCYANURATES AND VINYLIDENE CARBONYL OXY ALKANOLS" filed by Dr. Kenneth H. Markiewitz on July 27, 1977, the disclosure of which is hereby incorporated into the present application by reference. Briefly, this process is a two-step process which comprises a first step of reacting an aromatic polyisocyanate with a vinylidene carbonyl oxy alkanol in the presence of a copper salt, such as cupric acetate, to form an isocyanate-containing urethane and a second step of trimerizing the isocyanate-containing urethane in the presence of an isocyanate trimerization catalyst to form the ethylenically unsaturated isocyanurate composition of this invention.

The solution viscosity of the unsaturated isocyanurates of this invention can be varied over a wide range by adjusting the stoichiometry of the aromatic polyisocyanates and vinylidene carbonyl oxy alcohols employed in their synthesis and/or the temperature of the trimerization. Thus by varying the degree of the excess isocyanate groups compared to hydroxyl groups it is possible to adjust the formation of high molecular weight species and solution viscosities at a fixed concentration. Increasing the excess of isocyanate groups compared to hydroxyl groups favors higher molecular weight species and therefore higher viscosities, conversely lowering the excess isocyanate groups compared to hydroxyl groups favors lower molecular weight species and therefore lower viscosities. By appropriate adjustment of this excess a curable resin solution of the desired viscosity can be obtained. This may be done by experiment, realizing that higher solids concentration, and higher reaction temperatures also lead to resins of increased molecular weight and solution viscosity. The converse of this is also true. The excess of moles of NCO groups compared to moles of —OH per mole of polyisocyanate should be kept in the range from about 0.75 to about 1.6, and preferably from about 0.8 to about 1.4. In a solution comprising equal parts of solvent and a mixture of hydroxypropylmethacrylate and toluene diisocyanate, the excess of moles of NCO groups for laminate applications is preferably from about 0.8 to about 1.05.

The expression "excess of moles of NCO groups compared to moles of —OH per mole of polyisocyanate" means the excess of moles of NCO groups is equal to the moles of NCO used minus the moles of —OH used divided by the moles of polyisocyanate used.

The solution viscosity is also increased as the temperature used in the trimerization reaction increases, but this is not as important a variable as the excess of isocyanate groups compared to hydroxyl groups. However, the trimerization temperature is most often maintained from about 0° C. to about 95° C., since the trimerization reaction is slow at lower temperature and higher temperature may cause the vinylidene group to polymerize prematurely. A preferred trimerization temperature is from about 50° C. to about 90° C.

The particular trimerization temperature chosen will control the amount of allophanate remaining in the isocyanate composition. In general, the higher the temperature the lower the allophanate content. Allophanate-free isocyanurate may be prepared by conducting the trimerization at a temperature of above about 85° C. Allophanate-free isocyanurates may be prepared also by heating an allophanate-containing isocyanurate product of this invention to a temperature of, preferably, from about 85° C. to about 95° C. in the presence of a trimerization catalyst. Higher temperatures may be employed subject to the stability of the resin system. The isocyanurate products of this invention usually have an allophanate content sufficient to give an allophanate to urethane stoichiometric ratio of from about 0 to 0.7, and preferably from about 0 to 0.2, as determined by NMR measurements.

The characteristic of an allophanate free resin are (1) less evolution of gases when a peroxide and resin is heated and (2) longer shelf life of the uncured resin in the presence of unpromoted peroxides. Allophanate free resins may be prepared for the preparation of thick laminates in order to minimize gas evolution at elevated temperatures.

It will be readily apparent to one skilled in the art that some isocyanurate compositions of this invention may contain as a by-product urethanes which do not contain an isocyanurate ring. These urethanes may be formed by the reaction of all the isocyanate groups of the polyisocyanate used with hydroxyl groups from the vinylidene carbonyl oxy alkanol used. For example, isocyanurate composition of this invention made with tolylene triisocyanate and hydroxypropyl methacrylate may contain as a by-product the diurethane of one mole of tolylene diisocyanate and two moles of hydroxypropyl methacrylate. These urethanes may be characterized by the formula

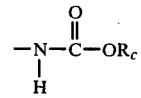

where $R_a$ is an aromatic radical free of a group which is reactive with an isocyanate group and is obtained by removing the isocyanate groups from an aromatic polyisocyanate, k is an integer which is equal to the number of isocyanate groups present in the polyisocyanate, and $R_b$ is $$-\underset{H}{\overset{}{N}}-\overset{O}{\overset{\|}{C}}-OR_c$$

where $R_c$ is a monovalent organic radical having the formula obtained by removing a hydroxyl group from a vinylidene carbonyl oxy alkanol characterized by formula (1) thru (5) recited above. The amount of such urethanes present in the compositions of this invention will depend mainly on the trimerization temperature and on the hydroxyl to isocyanate ratio used to prepare the isocyanurate composition. In general, the higher the trimerization temperature and/or the higher the ratio of hydroxyl groups to isocyanate groups, the higher will be the amount of such urethanes in the final product. In some cases the amount of such urethanes may amount to up to 65% by weight but more usually in the range of 10% to 50% by weight of the total composition.

Generally, as the solid content of the resin system decreases so does the solution viscosity, and to compensate for this reduction in viscosity which may make preparation of laminates a difficult task, the amount of high molecular weight polyisocyanurate structure is increased by increasing the excess of isocyanate groups to hydroxyl groups. The amount of these species may also be controlled by adjusting the trimerization temperature.

The following Table I illustrates ways to obtain vinylidene carbonyl oxy alkanol containing urethane isocyanurate solutions over a broad viscosity range. Although the table refers to the reaction products from hydroxypropylmethacrylate (HPMA) and toluene diisocyanate (TDI) dissolved in styrene, those skilled in the art will understand that similar relationships hold true for other solvent systems using other polyisocyanates or vinylidene alcohols. The examples in Table I illustrate the effect of the three important reaction parameters on the viscosity of the final product. Examples F and G as well as H and I show the effect of trimerization temperature on the viscosity of the final product. Examples D and F and J and L illustrate the effect of concentration on the viscosity, whereas, examples B and C, E, F, and I and also J and K demonstrate the effect of the molar excess of NCO groups compared to hydroxyl groups per mole of polyisocyanate, on the viscosity of the final product. All reactions listed in the table were carried to completion, i.e., the residual isocyanate content was essentially zero. Additional viscosity control may be achieved also by stopping the reaction short of completion as can be done in the usual manner by adding active hydrogen compounds compatible with the system and/or destruction of the trimerization catalyst. All reaction runs are in styrene using HPMA and TDI. Reaction runs B through L were made using the procedure outlined in example 1 whereas reaction run A was made according to the procedure outlined in example 8. The procedure used for run A involves a somewhat different mode of addition of polyisocyanate than used in runs B through L and is used primarily for the synthesis of low concentration products.

TABLE I

| | Moles (NCO)- Moles (OH) Moles Polyisocyanate | % Styrene | Trimerization Temperature (°C.) | Final Visc.[1] (cps) |
|---|---|---|---|---|
| A | 1.26 | 75 | 30 | 998(22.4° C.) |
| B | 1.16 | 70 | 45 | 395 |
| C | 1.20 | 70 | 45 | 10,000 |
| D | 1.10 | 60 | 55 | 370 |
| E | 1.22 | 50 | 55 | 17,000 |
| F | 1.10 | 50 | 55 | 2,200 |
| G | 1.10 | 50 | 25 | 1,050 |
| H | 1.00 | 50 | 75 | 790 |
| I | 1.00 | 50 | 55 | 450 |
| J | 0.95 | 40 | 55 | 1,400 |
| K | 0.91 | 40 | 55 | 800 |
| L | 0.97 | 30 | 55 | 66,000 |

[1]Determined on a Brookfield Viscometer, Model LVT, #2 spindle, at 30 rpm. at 25° C.

While it is essential that the isocyanurate compositions of this invention be based on one of the vinylidene carbonyl oxy alkanols defined above in order to obtain products having excellent high temperature properties, it is contemplated by the present invention that a minor amount of moieties derived from the vinylidene carbonyl oxy alkanols may be replaced with moieties derived from other monohydric alcohols, dihydric alcohols, monohydric phenols, or dihydric phenols. The saturated monohydric alcohols are especially useful with polyisocyanates of functionality greater than two. Although it has been found that the high temperature properties decrease as the amount of vinylidene carbonyl oxy alkanol decreases, one may be willing to sacrifice somewhat on the high temperature properties in order to introduce other desirable properties. For example, in some applications, one may be willing to sacrifice some high temperature properties for the inclusion of flame-retardancy or low smoke properties. The flame-retardance properties may be introduced by substituting a minor amount of the vinylidene carbonyl oxy alkanol with a phosphorus or florine, chlorine or bromine containing alcohol or phenol. Similarly, low smoke properties may be introduced by substituting a minor amount of the vinylidene carbonyl oxy alkanol with sulphur containing alcohols or phenols. While minor amount of any hydroxyl or phenolic material may be included in the isocyanurate compositions of this invention, it should be remembered that the isocyanurate compositions of this invention must be fusible and must meet the solubility test described above and must contain at least a major amount os isocyanurate moieties derived from a vinylidene carbonyl oxy alkanol described above.

Illustrative examples of monohydric alcohols and monohydric phenols which may be used to replace up to 49 mol percent of the vinylidene carbonyl oxy alkanols described above include: methanol, ethanol, propanol, butanol, isobutanol, octyl alcohol, cyclohexanol, benzyl alcohol, allyl alcohol, glycerol diallyl ether, trimethylolpropane diallyl ether, saturated halogenated alcohols, halogenated alcohols containing ethylenic unsaturation, for example, dibromoneopentyl glycol monoacrylate and monomethacrylate, halogenated allyl alcohols, monohydric alcohols such as 2-bromo ethanol, 3-bromo-1-propanol, 4-chloro-1-butanol, 2-chlorethanol, 4-chloro-1-hexanol, 3-chloro-1-propanol, 2,3-dibromo-1-propanol, 2,3-dichloro-1-propanol, 2,2,2-trichloroethanol, 1-bromo-2-propanol, 1-chloro-2-propanol, 1,3-dibromo-2-propanol, and 1,3-dichloro-2-propanol, mono acrylate and mono methacrylate esters of alkoxylated bisphenol A and alkoxylated tetra bromobisphenol A, and polyoxyethylene and polyoxypropylene ethers of monohydric phenols.

Illustrative examples of dihydric alcohols which may be used to replace up to 33 mol percent, and preferably up to 10 mol percent, of the vinylidene carbonyl oxy alkanols described above include: ethylene glycol, propylene glycol, polyethylene glycol, polypropylene glycol, compounds characterized by the formula:

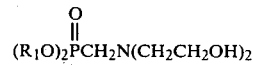

wherein $R_1$ is an alkyl group containing from 1 to 4 carbon atoms, 1,4-butane diol, pentamethylene glycol, hexamethylene glycol, glycerol methyl ether, polyoxyethylene and polyoxypropylene ethers of dihydric phenols such as bisphenol A, glycerol monochlorohydrin, glyceryl monostearate, dihydroxy acetone, and monoesters of the above polyols and acrylic acid or methacrylic acid.

In general, phenols in small amounts (up to 20 mole percent) that are reactive with aromatic isocyanates may be used in the practice of this invention. When reactive phenols are used, it is particularly important that essentially all of the phenolic hydroxyl groups are reacted with isocyanate groups so that unreacted hydroxyl groups will not be available to interfere with subsequent free radical curing reactions. Phenols such as 4-hydroxyphenyl 4'-chlorophenyl sulfone are especially useful because they characteristically improve the fire retardant and smoke properties of the product while still retaining elevated temperature retention of physical properties. Phenol may also be used to block a minor portion of the isocyanate functionality which may later be regenerated at elevated temperatures to produce products with improved bonding to a substrate, especially glass fibers. Nitrophenols do not react readily with isocyanates and are not within the scope of this invention.

The unsaturated isocyanurate compositions of this invention may be homopolymerized or copolymerized with one or more other ethylenically unsaturated copolymerizable compounds. Where the unsaturated isocyanurate composition of this invention is to be copolymerized with a copolymerizable monomer, the isocyanurate composition may be dissolved in the copolymerizable monomer or it may be desirable to utilize the copolymerizable compound as a solvent for the reaction system in which the ethylenically unsaturated isocyanurate compositions of this invention are formed. If the ethylenically unsaturated copolymerizable monomer is to be used as a solvent for the preparation of the unsaturated isocyanurate products, the solvent should not contain any groups which would react with isocyanate groups or in any way interfere with the urethane formation reactions or trimerization reactions which occur in the formation of the isocyanurate products of this invention. Thus, the solvent should not contain any hydroxyl, carboxyl, or amine groups which might interfere with these reactions. This limits the suitable solvents to esters, ethers, hydrocarbons and similar solvents containing non-reactive groups. Illustrative examples of solvents which may be employed in the preparation of the isocyanurate products of this invention include: divinyl benzene, styrene, methyl acrylate, methyl methacrylate, ethyl acrylate, ethyl methacrylate, 2-ethylhexyl acrylate, 2-ethylhexyl methacrylate, butyl acrylate, butyl methacrylate, cyclohexyl acrylate, cyclohexyl methacrylate, chlorostyrene, acrylonitrile, vinylidene chloride, vinyl acetate, vinyl stearate, vinyltolylene, hexanediol diacrylate, hexanediol dimethacrylate, tetrahydrofurfuryl methacrylate, diethylene glycol diacrylate, triethylene glycol diacrylate, allyl methacrylate, diallyl fumarate, tetramethylene glycol diacrylate, trimethylolpropane triacrylate, neopentyl glycol diacrylate, 1,3-butylene glycol diacrylate, 1,3-butylene glycol dimethacrylate, polyethylene glycol diacrylate, dimethylstyrene, ethylstyrene, propylstyrene, parachloromethyl styrene, meta-dibromoethyl styrene, bromo styrene, dichloro styrene, t-butyl styrene, vinyl propionate, and vinyl butyrate. Nonpolymerizable solvents may also be used, for example, benzene, toluene, xylene, and ethylbenzene. The solvent may be removed from the reaction mixture after the formation of the isocyanurate to give a solid product. The solid product may be dissolved in the same or a different polymerizable solvent prior to curing. Mixtures of solvents may also be used. Preferred solvents are styrene, a mixture of styrene and methyl methacrylate, and a mixture of styrene and divinylbenzene.

When the isocyanurates of this invention are prepared in the absence of solvent, the product formed is a solid and requires special processing which permits the easy removal of the heat generated by the reaction and which prevents the reaction mixture from reaching high temperatures which may induce insolubility and gelation of the products. Among these special processing techniques may be the trimerization of the monourethane in thin layers on moving temperature-controlled belts or in temperature-controlled trays.

The amount of solvent employed to dissolve the isocyanurate compositions of this invention may vary over a very wide range. The particular amount of solvent used will depend somewhat on the nature of the solvent and on the solubility of the particular isocyanurate used. The polymeric character of the isocyanurate product allows maintenance of adequate working viscosity at relatively low concentrations of dissolved solids. Products of this invention may be made which permit adequate laminate working viscosity, which is defined as 100 to 1,000 centipoises Brookfield as determined on a Brookfield Viscometer, Model LVT, #2 spindle, at 30 rpm., at 25° C. The amount of solvent will also depend on the nature of the properties desired in the final cured product. Thus, if one is interested in preparing a copolymer of styrene and an isocyanurate of a monourethane of tolylene diisocyanate and hydroxypropyl methacrylate, for example, the high temperature properties of the final product will increase as the concentration of the styrene decreases. In general, however, the amount of solvent used will be from 5 to 95 weight percent of the total composition and preferably from 30% to 80% by weight of the total composition. A particularly preferred concentration is about 50% by weight.

The unsaturated isocyanurate compositions prepared by the process of this invention and solutions thereof in copolymerizable solvent may be polymerized or cured in accordance with polymerization conditions conventional in the art for the polymerization of ethylenically unsaturated materials. Isocyanurates of this invention, particularly styrene solutions of isocyanurates made with tolylene diisocyanates or polymethylene polyphenylene polyisocyanate and hydroxyl propyl methacrylate, hydroxyl ethyl methacrylate, or hydroxyl propyl acrylate, are less sensitive to oxygen than conventional vinyl systems in yielding tack-free surfaces. In general, the polymerization may be carried out by reacting the unsaturated isocyanurate in the presence of a polymerization catalyst. Suitable polymerization initiators include the various peroxide initiators such as benzoyl peroxide, methyl ethyl ketone peroxide, di(2-ethylhexyl) peroxydicarbonate, t-butyl perbenzoate, dicumyl peroxide, and t-butyl hydroperoxide. Other polymerization catalysts which may be used include azo type initiators such as azobisisobutyronitrile. The amount of initiator employed is usually very small. For example, from about 1 part of initiator per 1000 parts of the polymerizable mixture to about 5 parts per 100 parts of said mixture.

In many applications, it is desirable to start the polymerization without the application of external heat. In such cases it is customary to add an accelerator to the system. Suitable accelerators include cobalt, manganese, lead, and iron compounds, such as cobalt naphthenate and manganese naphthenate, and tertiary amines such as dimethyl aniline.

The following are three illustrative examples of peroxide-promoter formulations which may be used to cure the unsaturated isocyanurates of this invention:
Formulation I
1% Benzoyl peroxide
0.2% Dimethyl aniline
Formulation II
0.02% Dimethyl aniline
0.06% Cobalt naphthenate
2.0% Methyl ethyl ketone peroxide
Formulation III
0.03% Cobalt naphthenate
0.5% Acetylacetone peroxide (4% active oxygen)
1.5% t-butyl perbenzoate In order to avoid premature polymerization of the isocyanurate composition of this invention, a small amount of a cupric salt such as cupric acetate, or a conventional polymerization inhibitor, such as hydroquinone, methyl ether of hydroquinone, phenothiazine, and tertiary butyl catechol, may be incorporated either into the reaction mixture prior to preparation of the isocyanurate product or into the final product or both.

The resulting isocyanurate product, particularly when prepared as a solution in a copolymerizable monomer, may contain any of the additives which are conventionally employed in polymerization systems, for example, antioxidants, U.V. absorbers, dyes and pigments.

The unsaturated isocyanurate products of this invention have been found to be particularly useful in applications such as castings, coatings, and laminates where it is desirable to have excellent flexural and tensile properties and good corrosion resistance at elevated temperatures. Laminates prepared with wettable fibers preferably contain at least 20% by weight of isocyanurate composition and up to 80% by weight of wettable fiber. Cured products obtained from polymerizing concentrated isocyanurate solutions of this invention exhibit thermal stability at temperatures above 325° F.

The products of this invention may be used alone or in combination with other ethylenically unsaturated monomer compositions. In addition, these products may be used in combination with inorganic fillers, such as calcium carbonate, magnesium oxide, alumina trihydrate; organic polymers such as polyethylene, polymethylmethacrylate and other additives to reduce shrinkage; and fire retardant additives or other polymerizable resins, such as general purpose polyester resins. The products of this invention are especially useful when used in combination with glass fibers, cellulosic fibers, aramide fibers, or other fibers to produce reinforced structures, such as laminates and pipe. The products of this invention exhibit excellent wettability when used with these fibers.

The invention will be better understood from a consideration of the following examples which are presented for illustrative purposes and are not to be considered as defining or limiting the scope of this invention. All parts and percentages are by weight unless otherwise specified.

In the following examples, the castings and laminates are prepared as follows:

Castings are prepared by pouring the isocyanurate solution containing the curing reagents between two sheets of plate glass separated by a ⅛" polytetrafluoroethylene covered wire spacer. The curing reagents are added to the solution of isocyanurate in copolymerizable solvent by first adding the indicated promoter and accelerator to the isocyanurate solution and then adding the indicated peroxide. The casting is maintained at room temperature for 18-24 hours and then the resin is heated one hour at 100° C. in an oven to undergo postcuring;

Laminates are prepared by rolling the indicated isocyanurate solution containing the curing reagents evenly onto glass fiber mats with a paint-type roller then rolling thoroughly with a grooved laminating roller. The curing reagents are added to the solution of isocyanurate in copolymerizable solvent by first adding the indicated promoter and accelerator to the isocyanurate solution and then adding the indicated peroxide. ⅛" thick laminates are prepared with two layers of split strand 1½ ounce glass mats sandwiched between two 10 mil. surfacing "C" glass mats. The weight of the glass is 25% of the total resin glass weight. ¼ inch thick laminates are made by the following combination of glass mats impregnated with resin: 10 mil. surfacing "C" glass mat, two layers of 1½ ounce chopped strand mat, 1 layer woven roving, one layer of 1½ ounce chopped strand mat, 1 layer of woven roving and a final layer of 1½ ounce chopped strand glass mat. The amount of resin used to make this ¼" laminate is adjusted to give a resin ratio of 70%. Laminates are covered with a thin polyester film to exclude air from the surface during cure. After 18-24 hours at room temperature the cured laminates are heated for 1 hour at 100° C. in an oven for postcure.

Physical properties of the castings and laminates prepared in the following examples are measured by the indicated ASTM test methods:

| Physical Property | ASTM Test Method |
|---|---|
| Flexural strength | D 790 |
| Flexural modulus | D 790 |
| Tensile strength | D 638 |
| Tensile modulus | D 638 |
| % Elongation | D 638 |
| Izod Impact strength | D 256 |
| Barcol Hardness | D 2583 |
| Heat Deflection Temperature (264 psi) | D 648 |

EXAMPLE 1

A three-neck, round-bottom, 5-liter glass flask, equipped with thermometer, air inlet, dropping funnel, and condenser is charged with 865 ml of hydroxypropyl methacrylate, 2144 ml of styrene, 1.8 g of cupric acetate, and 800 mg of hydroquinone. The solution is heated to 85° C., and 852 ml of toluene diisocyanate are slowly added over a 150 min. period. The temperature of the reaction medium during the addition of the toluene diisocyanate is maintained between 88° C. and 90° C. After the addition of the toluene diisocyanate is complete, the temperature of the reaction mixture is maintained at about 90° C. for an additional 90 min. The resulting dark green liquid is cooled to 55° C., and 5 ml of a 40% solution of benzyltrimethylammonium hydroxide dissolved in methanol is added over a 13 min. period. Heating is then continued at 55° C. for 2 hrs. to form an ethylenically unsaturated isocyanurate.

EXAMPLE 2

611.0 g of styrene, 33.1 g of hydroxypropyl methacrylate, 225 mg of cupric acetate, 100 mg of hydroquinone, are added to the reaction vessel described in Example 1. The resulting solution is heated to 90° C. while stirring vigorously. At this point, 34.8 g of toluenediisocyanate are added dropwise at a rate of approximately 6 to 10 ml/min. to the reaction flask. The temperature of the reaction medium is maintained at 90° C. until the addition of the toluenediisocyanate is complete and then for an additional 40 min. The resulting clear, emerald green solution is cooled to 55° C., and 1.5 ml of a 40% solution of benzyltrimethylammonium hydroxide in methanol is added. The solution remains unchanged for several minutes then begins to turn brown. The temperature of the solution is maintained at 55° C. until the isocyanate content falls to about 0. The resulting product is a styrene solution of the ethylenically unsaturated isocyanurate of toluene diisocyanate and hydroxypropyl methacrylate.

Examples 3–5 are prepared according to the process recited in Example 2 except that the amounts of styrene, hydroxypropyl methacrylate (HPMA), hydroxyethyl methacrylate (HEMA), and toluene diisocyanate (TDI) used are those indicated in the following Table I.

TABLE I

| Example Number | Styrene (grams) | HPMA (grams) | HEMA (grams) | TDI (grams) |
|---|---|---|---|---|
| 3 | 282 | 0 | 70.8 | 87 |
| 4 | 214 | 0 | 99.5 | 115.8 |
| 5 | 240 | 109.9 | 0 | 130.5 |

EXAMPLE 6

According to the process of Example 1, 1314 grams of styrene, 232 grams of hydroxypropyl methacrylate, 4 ml. of a 10% solution of tertiary butyl catechol in styrene, and 920 milligrams of cupric acetate monohydrate are heated to 90° C. under an air sparge and nitrogen blanket and 335 grams of toluene diisocyanate (25% excess) are then added slowly over 60 minutes. The temperature is maintained at 90° C. during the addition and for 60 minutes afterward. The product is cooled to 41° C. and 5 ml. of 4% benzyltrimethylammonium hydroxide (Triton B) in methanol are added. The temperature is maintained at 45° C. for 4 hours. 5 ml. of tertiary butyl catechol (10% solution in styrene) and 1.05 ml. of methanesulfonic acid are added and the product is cooled. The resulting polymeric, ethylenically unsaturated polyisocyanurate contains a high proportion of product of molecular weight about 200,000 as determined by gel permeation chromatography. The viscosity after sitting overnight at room temperature is about 10,000 centipoise.

EXAMPLE 7

A 3-liter, 4-neck flask equipped with temperature control, air sparge, $N_2$ blanket, condenser, addition funnel, and stirrer is charged with 1254 grams of styrene, 227 grams of hydroxypropyl methacrylate (hydroxyl number 364), 460 milligrams of cupric acetate monohydrate, and 4.0 ml. of 10% tertiary butyl catechol (TBC) in styrene. The flask was then heated to 90° C. and 313 grams of toluene diisocyanate (TDI) is dripped in over a 55 minute period while the temperature is maintained at 90°–98° C. At the end of the TDI addition the temperature is maintained at 90° C. for an hour and a half, after which the solution is cooled to 45° C. 5 cc. of a 40% solution of benzyltrimethylammonium hydroxide in methanol is added. The resin turns very dark and an exotherm occurs which is controlled by means of a water bath so that the temperature does not exceed 50° C., and is restored to 45° C. and is maintained there. After 3.1 hours 1.20 cc. of methanesulfonic acid is added and a cooling water bath is applied. At 30° C. 5 ml. of 10% t-butyl catechol solution in styrene is added. At 25° C. the resin is poured into cans. The Brookfield viscosity is 395 cps. at 25° C. Physical properties are measured on a ⅛" casting that is postcured at 100° C. for 1 hour. The cure system comprises 100 grams resin, 0.4 gram dimethyl aniline, 0.5 gram cobalt naphthenate, 0.5 gram Lupersol 224 (acetylacetone peroxide solution), and 1.5 grams tertiary butyl perbenzoate. The casting (30% solids in styrene) has the following physical properties:

Tensile modulus (psi) $0.49 \pm 0.03 \times 10^6$
Tensile strength (psi) 10,900
% Elongation 2.58
Flexural strength (25° C., psi) 17,300
Flexural modulus (psi) $0.53 \times 10^6$
Heat distortion temperature 111° C.
Unnotched izod impact 2.91

EXAMPLE 8

A 3-liter, 4-neck flask is equipped with mechanical stirrer, the thermometer, air sparge, reflux condenser, and $N_2$ inlet is charged with 171.0 grams hydroxypropyl methacrylate (1.14 equiv.), 1315.8 grams styrene (12.64 equiv.), 0.4535 gram $Cu(OAc)_2 \cdot H_2O$, and 3.75 ml. 10% tertiary butyl catechol (TBC) in styrene solution and the mixture is heated while stirring to 90° C. 206.9 grams toluene diisocyanate (TDI) (1.19 equiv.) is added dropwise over a 1 hour period, while maintaining the temperature at 90°±5° C. The reaction mixture is kept at 90°±5° C. for an additional hour, then cooled over a 1 hour period to 35° C. After adding 62.1 grams TDI (0.36 equiv.), it is cooled further to 30° C. 4.8 ml. benzyltrimethylammonium hydroxide (40% is MeOH) is then added, causing an exotherm which is controlled by use of a water bath. The trimerization reaction is terminated after 2.6 hours by addition of 14.9 grams dibutylamine; after 15 minutes, 1.49 ml. methanesulfonic acid (MSA) is added. The resulting product has a viscosity of 998 cps. at 22.4° C. A ⅛" casting is made and cured according to the method described in Example 7. The casting (25% solids in styrene) has the following properties:

Tensile modulus (psi) $0.55 \times 10^6$
Tensile strength (psi) 9,400
% Elongation 2.28
Flexural strength (psi) 16,700
Unnotched izod (ft-lbs) 2.97
Heat distortion temperature 221° F.
Flexural modulus (psi) $0.85 \times 10^6$

EXAMPLE 9

Into a 3-liter, 4-neck flask equipped with mechanical stirrer, thermometer, air sparge, reflux condenser, and nitrogen inlet is charged methyl methacrylate (892 grams, 8.91 moles), hydroxypropyl methacrylate (414 grams, 2.78 moles), copper acetate monohydrate (0.403 gram), and 10% tertiary butyl catechol/styrene solution (4.0 cc.). The mixture is stirred and heated to 90° C., and toluene diisocyanate (TDI) (468 grams, 2.69 moles) added slowly over two hours while maintaining the temperature at 90° C. After all the TDI is added, the temperature is maintained at 90° C. for an hour while stirring and the reaction mixture is then cooled to 50° C. Triton B (40% benzyltrimethylammonium hydroxide in methanol) (5.0 ml.) is added. An exothermic reaction occurs and the temperature of the reaction mixture is maintained at 55° C. by external cooling. After keeping the mixture at 55° C. for two hours, it is then cooled to room temperature and 1.2 ml. methanesulfonic acid added. The resin has a viscosity of 1050 cps. at 23° C. A ⅛" casting is made and cured according to the method of Example 7. A ⅛" laminate is prepared using two plies of 1½ ounce chopped fiberglass strand mat between two 10 mil. surfacing "C" glass mats and cured at 100° C. for one hour. The casting and laminate have the following properties:

|  | ⅛" Casting | 25% glass laminate ⅛" thick |
|---|---|---|
| Tensile modulus (psi) | $0.60 \times 10^6$ | $1.41 \times 10^6$ |
| Tensile strength (psi) | 8,500 | 14,800 |
| % Elongation | 1.65 | 1.47 |
| Flexural modulus (psi) | $0.60 \times 10^6$ | $0.80 \times 10^6$ |
| Notched izod (ft-lbs) | — | 5.51 |
| Heat deflection temperature | 266.9° F. | — |
| Flexural strength (300° F., psi) | — | 14,000 |
| Flexural modulus (300° F., psi) | — | $0.51 \times 10^6$ |
| Barcol (300° F.) | — | 21–24 |
| Barcol (room temperature) | 55–62 | — |
| Flexural strength (psi) | 15,100 | 16,500 |

EXAMPLE 10

A 3-liter, 4-necked flask equipped with a mechanical stirrer, thermometer, air sparge, reflux condenser, dropping funnel and nitrogen inlet is charged with hydroxypropyl methacrylate (414 grams, 2.8 moles), styrene (772 grams, 7.4 moles), divinylbenzene (124 grams of a 72% active solution, 0.68 moles), cupric acetate monohydrate (0.45 gram), and 20% solution of tertiary butyl catechol in styrene (2 ml.). The mixture is heated to 40° C. and toluene diisocyanate (TDI) (80/20 mixture of 2,4- and 2,6-isomers, 486 grams, 2.8 moles) added over one hour. The reaction temperature is gradually increased to 90° C. by a combination of external heat and the exothermic nature of the reaction. The reaction mixture is kept at 90° for an additional hour and then cooled over ninety minutes to 45°±5° C. Triton B (40% solution of benzyltrimethylammonium hydroxide in methanol, 5 ml.) is then added and the exotherm controlled by use of a water bath. The reaction mixture is kept at 55°±5° C. for 2.5 hours and the trimerization reaction terminated by addition of methanesulfonic acid (1.2 ml.). The product has a viscosity of 1060 cps. at 21° C. A laminate is prepared and cured according to the method used in Example 9. The cured laminate has a flexural strength of 18,800 psi at room temperature and 11,100 psi at 350° F.

EXAMPLES 11-17

The procedure and apparatus for Example 1 are used in Examples 11-17. The indicated amount of toluene diisocyanate is added dropwise under a nitrogen blanket and air sparge to the copper catalyst, t-butyl catechol, and unsaturated alcohol in styrene at about 90° C. When the NCO content has dropped to about half the original content, the solution is cooled to about 55° C., Triton B added, and stirring is continued until the reaction is complete. The methanesulfonic acid and/or the TBC is then added to stabilize the product resin solution. The specific reactants, solvent, and catalysts used and the amounts thereof are shown in Table II.

TABLE II

| Example Number | Grams TDI | Grams Alcohol | Unsatd. Alcohol | Grams Solvent | Solvent | Grams Cupric Acetate Monohydrate |
|---|---|---|---|---|---|---|
| 11 | 129 | 82.2 / 28.8 | HPMA PETA | 358 | styrene | 0.23 |
| 12 | 519.8 | 260 / 218 | HPMA DBP | 1000 | styrene | 0.92 |
| 13 | 519.8 | 288 / 324.84 | HPMA TBNA | 1134.8 | styrene | 1.09 |
| 14 | 150.8 | 63.97 / 188 | HPMA[1] | 402.9 | styrene | 0.387 |
| 15 | 173.2 | 72 / 400 | HPMA[2] | 616 | styrene | 0.597 |
| 16 | 173.2 | 117.6 / 53.8 | HPMA[3] | 345.4 | styrene | 0.36 |
| 17 | 520 | 220.5 / 220.5 | HPMA HEMA | 954.9 | styrene | 0.92 |

| Example Number | cc. 10% t-butyl catechol-styrene | cc. Triton B | cc. Methanesulfonic acid | % Solids | % Unreacted —NCO Group | Product Viscosity In cps at Room Temp. |
|---|---|---|---|---|---|---|
| 11 | 1 | 1 | 0.3 | 40 | 3.9 | 20,000[4] |
| 12 | 4 | 5 + 2 + 2 | 1.5 | 50 | 8.7 | — |
| 13 | 5 | 5 | 1.5 + 5 TBC | 50 | 6 | 720 |
| 14 | 2 | 3 | — (3 TBC) | 50 | 7 | — |
| 15 | 3 | 3 | — (3 TBC) | 50 | 5 | 4400[5] |
| 16 | 3 | 2 | 1 + 4 TBC | 50 | 2 | 1500 |
| 17 | 4 | 5 | — (5 TBC) | 50 | 0 | 360 |

HPMA = hydroxypropyl methacrylate
PETA = pentaerythritol triacrylate
DBP = 2,3-dibromopropanol
TBNA = tribromoneopentyl alcohol
HEMA = hydroxyethyl methacrylate
TBC = t-butylcatechol (10% in styrene)
Triton B = benzyltrimethylammonium hyroxide (40% in methanol)
TDI = toluene diisocyanate
[1]monomethacrylate of 2,2-polyoxypropylenebisphenol A
[2]monomethacrylate of 2,2-polyoxypropylene tetrabromobishphenol A
[3]4-hydroxy-4'-chlorodiphenyl sulfone
[4]diluted with 26.25 g. HPMA and 17.4 g. styrene to 37% solids, viscosity 1150 cps
[5]diluted with 7.2 t. HPMA, viscosity 2600 cps

EXAMPLES 18-20

Examples 18-20 are prepared according to the process of Example 17 except that the indicated amounts of toluene diisocyanate, unsaturated alcohol, solvent and catalyst used are those indicated in Table III.

TABLE III

| Example Number | Grams TDI | Grams Alcohol | Unsatd. Alcohol | Grams Solvent | Solvent | Grams Cupric Acetate Monohydrate |
|---|---|---|---|---|---|---|
| 18 | 228.8 | 169.8 | HPA | 398.6 | styrene | 0.4 |
| 19 | 519.7 | 441 | HPMA | 700 / 262 | styrene MMA | 0.92 |
| 20 | 494 | 441 | HPMA | 307 | MMA | 0.92 |

| | cc. 10% | cc. | | % Unreacted | Product Viscosity |

TABLE III-continued

| Example Number | TBC-styrene | Triton B | cc. MeSO₃H | % Solids | —NCO Group | In cps at Room Temp. |
|---|---|---|---|---|---|---|
| 18 | 1 | 3 | — | 50 | 0 | 10,600 |
| 19 | 4 | 5 | — (5 TBC) | 50 | 0 | 350 |
| 20 | 4 | 5 | 1.5 + 5 TBC | 75 | 0 | (high)[2] |

TDI = toluene diisocyanate
TBC = t-butylcatechol (10% in styrene)
Triton B = benzyltrimethylammonium hydroxide (40% in methanol)
MeSO₃H = methanesulfonic acid
HPA = hydroxypropyl acrylate
HPMA = hydroxypropyl methacrylate
MMA = methyl methacrylate
[1]200 mg. hydroquinone
[2]diluted with 252 g. MMA, viscosity 725 cps

EXAMPLES 21–26

The procedure of Example 17 is used in Examples 21–26. The indicated reactants, catalysts and solvent and the amounts used are shown in Table IV.

EXAMPLES 27–34

The isocyanurate products of Examples 27–34 are prepared according to the procedure of Example 1, except for the variations in reactants, solvent and cata-

TABLE IV

| Example Number | Grams Isocyanate | Isocyanate | Grams HPMA | Grams Styrene | Ratio Alc./—NCO | Grams Cupric Acetate Monohydrate |
|---|---|---|---|---|---|---|
| 21 | 176 | Mondur MR | 125 | 122 | 1:1.6 | 0.268 |
| 22 | 184.2 | Isonate 125M | 115.8 | 298 | 1:1.9 | 0.23 |
| 23 | 190.9 | Isonate 143L | 109.1 | 298 | 1:1.8 | 0.23 |
| 24 | 216.6 | Takenate 500 | 147.4 | 238 | 1:2.3 | 0.23 |
| 25 | 238 213.2 | Mondur MR TDI | 372.5 | 813 | 1:1.7 | 0.92 |
| 26 | 528 | PAPI | 400 | 928 | 1:1.6 | 0.84 |

| Example Number | cc. 10% TBC in Styrene | cc. Triton B | cc. MeSO₃H | % Solids | % Unreacted —NCO | Product Viscosity In cps at Room Temp. |
|---|---|---|---|---|---|---|
| 21 | 1 | 1 | 0.3 + 1 TBC | 50 | 5.6 | 495 |
| 22 | 1 | 0.5 | 0.2 + 1 TBC | 50 | 3.1 | 473 |
| 23 | 1 | 1 | 0.3 + 1 TBC | 50 | 1.5 | 1825 |
| 24 | 1 | 2 | 0.6 + 1 TBC | 60 | 6.5 | 305 |
| 25 | 4 | 5 | — (6 TBC) | 50 | 3.0 | 1275 |
| 26 | 3.6 | 5 | — (4 TBC) | 50 | 5.2 | 135 |

HPMA = hydroxypropyl methacrylate
TBC = t-butylcatechol (10% in styrene)
Triton B = benzyltrimethylammonium hydroxide (40% in methanol)
MeSO₃H = methanesulfonic acid
Mondur MR = diphenylmethane contg. 2.6 isocyanate groups avg.
Isonate 125M = diphenylmethane contg. 2.0 NCO groups avg.
Isonate 143L = diphenylmethane contg. 2.1 NCO groups avg.
Takenate 500 = 1,3-xylene-4,6-diisocyanate
TDI = toluene diisocyanate
PAPI = polyphenylenepolymethylene polyisocyanate contg. 2.2 NCO groups avg.

lysts indicated in Table V.

TABLE V

| Example Number | Grams TDI | Grams HPMA | Grams Styrene | Grams Copper Salt | Copper Salt | cc. 10% TBC in styrene |
|---|---|---|---|---|---|---|
| 27 | 170.5 | 147 | 318.3 | 0.307 | chloride | 1 |
| 28 | 520.2 | 441 | 962 | 1.0 | naphthenate | 4 |
| 29 | 161.1 | 138.9 | 298 | 0.72 | nitrate | 1 |
| 30 | 520.2 | 441 | 954.9 | 0.92 | acetate | 4 |
| 31 | 130 | 110 | 238.7 | 0.92 | acetate | 1 |
| 32 | 130 | 110 | 238.7 | 0.92 | acetate | 1 |
| 33 | 520.2 | 440 | 961.6 | 0.92 | acetate | — (0.4 HQ) |

TABLE V-continued

| 34 | 520.2 | 441 | 954.9 | 0.92 | acetate | 2 |

| Example Number | Trimerization Catalyst | Trimerization Catalyst | cc. MeSO$_3$H | % Solids | % Unreacted —NCO Group | Product Viscosity In cps at Room Temp. |
|---|---|---|---|---|---|---|
| 27 | 1 cc. | Triton B | 0.3 | 50 | 4.6 | 222.5 |
| 28 | 5 cc. | Triton B | — (5 TBC) | 50 | 2.3 | 1600 |
| 29 | 5 cc. | Triton B | 1.5 | 50 | 0.33 | 395 |
| 30 | 2.5 cc. | Polycat 41 | — (5 TBC) | 50 | 6.2 | 800 |
| 31 | 1.25 cc. | Me$_4$N.OH | 0.375 + 1.25 TBC | 50 | 2.6 | 410 |
| 32 | 0.5 g | Et$_4$N.O$_2$CH | 0.375 + 1.25 TBC | 50 | 3.1 | 280 |
| 33 | 5 cc. | KOAc | — (0.5 HQ) | 50 | 0 | — |
| 34 | 2.0 g. | Et$_4$N.OAc | 1.5 + 2.5 TBC | 50 | 2.8 | 350 |

TDI = toluene diisocyanate
HPMA = hydroxypropyl methacrylate
MeSO$_3$H = methanesulfonic acid
Triton B benzyltrimethylammonium hydroxide (40% in methanol)
Polycat 41 = a polyfunctional aliphatic tertiary amine (Abbott)
Me$_4$N.OH = tetramethylammonium hydroxide (40% in methanol)
Et$_4$N.O$_2$CH = tetraethylammonium formate
KOAc = potassium acetate
Et$_4$N.OAc = tetraethylammonium acetate
TBC = t-butylcatechol (10% in styrene)
HQ = hydroquinone

EXAMPLE 35

A preferred method of preparing an isocyanurate composition of this invention containing allophanate groups is as follows. A chemical reactor equipped with agitator, condenser, gas pipe connections, vents and port holes is first flushed with subsurface nitrogen. Subsequently an air sparge and nitrogen stream having relative flow rates of 1 to 3 are introduced into the reactor. 2.7 parts of hydroxypropylmethacrylate (HPMA) are then charged to the reactor. The air sparge and nitrogen streams are temporarily turned off and 0.0029 parts of copper acetate monohydrate and 0.012 parts of 20% solution of tertiary butyl catechol (TBC) in styrene are charged to the reactor under continuous agitation. The air sparge and nitrogen blanket streams are turned on again and 5.7 parts of styrene are charged to the reactor. The reaction mixture is then heated to about 40° C. When the temperature of the reaction mixture reaches 40° C. the incremental addition of an 80/20 mixture of 2,4- and 2,6-toluene diisocyanates (TDI) starts. An overall amount of 3.1 parts of TDI are charged over about one hour period. During this period the exotherm of the reaction of TDI with the alcohol raises the temperature of the reaction mixture to about 90° C. If at the end of the TDI addition the temperature is lower or higher than 90° external heating or cooling is applied respectively to bring the temperature to about 90° C. The reaction mixture remains at about 90° C. for at least one hour after the total amount of TDI has been added and until the NCO content of the reaction mixture drops to below 4.5% by weight. After both conditions are met the reaction mixture is cooled to about 50° C. 0.018 parts of 40% solution of benzyltrimethylammonium hydroxide in methanol (Triton B) (a trimerization catalyst), are then added to the reaction mixture. Soon after the addition of Triton B an exothermic reaction starts during the duration of which the temperature of the reaction mixture is maintained between 50°–60° C. From the time the exotherm appears the viscosity and NCO content of the reaction mixture are monitored very closely. When the viscosity of the reaction mixture reaches 400–500 cps and the NCO level drops to below 0.2%, 0.007 parts of methanesulfonic acid are added to the reaction mixture and the mixture is then cooled. When the temperature reaches about 35° C., 0.014 parts of TBC are added and the reaction is then cooled to room temperature. The resulting vinyl isocyanurate is clear, has a light yellow brown color, a viscosity of about 400–500 cps and a shelf life longer than 3 months. Laminates are prepared from this isocyanurate solution using a curing system of 0.2% dimethylaniline, 0.2% tertiary butyl catechol, and 2.0% benzoyl peroxide solution (50% active). ⅛" 2-ply laminates prepared from this resin retain more than 80% of their room temperature flexural and tensile strength at 300° F.

The reaction product has a number average molecular weight of about 1160, a weight average molecular weight of about 2000, and a polydispersity of about 1.9. About 95% of the isocyanurates present have a molecular weight of below about 5200 and contain some isocyanurates having a molecular weight about 5200 and below about 26,000. This product corresponds to a product of formula II above where the number of isocyanurate rings in most of the isocyanurate molecules is less than 10. This product has a ball and ring melting point of about 95° C. and a viscosity of about 400–600 cps at 25° C., and a refractive index of about 1.557 N$_D^{20}$. The infra-red spectrum of this product shows absorption bands characteristic of isocyanurates and the essential absence of isocyanate functionality. The hydroxyl number of the product is essentially zero.

⅛" 2-ply laminates prepared from this resin retain more than 80% of their room temperature flexural and tensile strength at 300° F. The curing reagents used to cure the resin are 0.2% dimethyl aniline, 0.2% of a 10% solution of tertiary butyl catechol in styrene, and 2.0% benzoyl peroxide (50% active).

EXAMPLE 36

To a solution of 307 grams of a mixture of 1- and 2-hydroxydecyl methacrylate in 481 grams methyl methacrylate is added 0.3 grams of cupric acetate monohydrate and 1.3 ml. of 10% solution of t-butyl catechol in methyl methacrylate. The solution is heated to 90° C. and 174 grams of toluene diisocyanate added during 30 minutes. The temperature is maintained at 90° C. for an additional one hour. The solution is cooled to 55° C. and 1.7 ml. of a 40% methanolic solution of benzyltrimethylammonium hydroxide is added. The reaction is completed by heating for an additional 3 hours at 60° C. The reaction is terminated by the addition of 1.7 ml. 10% solution of t-butyl catechol in methyl methacrylate and 0.5 ml. methanesulfonic acid.

EXAMPLE 37

To a solution of 165 grams of 2-hydroxybutyl methacrylate in 71 grams of styrene is added 313 mg. of cupric acetate monohydrate and 0.75 ml. of a 10% solution in styrene of a 50/50 mixture of t-butyl catechol and mono-methyl ether of hydroquinone. The solution is heated to 90° C. and 174 grams of toluene diisocyanate is added over one hour. Heating at 90° C. is continued for one hour. Then 268.3 grams of additional styrene is added, the solution cooled to 55° C., and 2.5 ml. of a 40% methanolic solution of benzyltrimethylammonium hydroxide added. The solution is maintained at 55° C. for one hour. The reaction is terminated by the addition of 1.3 ml. of a 10% solution in styrene of a 50/50 mixture of t-butyl catechol and mono-methyl ether of hydroquinone. The product has a viscosity of 200 cps at 25° C. Two-ply glass laminates (25% glass, 0.125 inch thick) of the resulting 50% resin solution in styrene and which are cured with 0.1% dimethylaniline, 0.5% acetylacetone peroxide solution (4% active oxygen), 1.5% tertiary butyl perbenzoate, and 0.1% of a 10% solution of tertiary butyl catechol in styrene, have the following physical properties measured at 300° F.: flexural strength 17,600 psi; flexural modulus $0.48 \times 10^6$ psi; tensile strength 11,900 psi; tensile modulus $0.66 \times 10^6$ psi; Barcol hardness 25–28; elongation 2.2%; notched Izod 4.05.

EXAMPLE 38

Into a 2-liter 3-neck flask equipped with mechanical stirrer, thermometer, and air sparge is charged toluene diisocyanate (TDI) (80/20 mixture of 2,4- and 2,6- isomers, 342 ml., 2.44 mole) and the contents of the flask are heated to 55° C. A solution consisting of copper acetate monohydrate (0.4 grams) and 3.0 ml. of a 10% tertiary butyl catechol in toluene solution, w/w, in hydroxypropyl methacrylate (360 ml., 2.44 mole), having an acid number of 18, is added dropwise from an addition funnel over a period of 31 minutes into the TDI. 49.4% of the original isocyanate concentration remains unreacted (analysis by infra-red spectrophotometer) while the resulting green mixture has a viscosity of 550 cps. 2.5 ml. of a 20% tertiary butyl catechol in toluene solution, w/w, and Triton B (40% benzyltrimethylammonium hydroxide in methanol), (0.8 ml.) are added to 150 grams of the above mixture at 40° C. The mixture is stirred vigorously and placed in a pan submerged in a constant temperature bath at 45° C. After 12 minutes bubbles begin forming on the surface of this green mixture and after 35 minutes the color begins changing to brown. Concurrently, the temperature rises to 84° C. in 16 minutes and the product solidifies. The product is allowed to cool to 40° C. and then removed from the pan to be ground into a fine powder. The product is then dissolved in an equal weight of styrene, 1.5% tertiary butyl perbenzoate, 0.5% of a 6% solution of cobalt naphthenate, and 0.4% dimethylaniline are added and then 0.5% of acetylacetone peroxide solution (4% active oxygen) is added to the solution. The solution containing the curing reagents is used for the preparation of a ⅛″ laminate containing about 25% glass. The physical properties of the laminate are as follows:

| Property | Temperature | |
|---|---|---|
| | 73° F. | 300° F. |
| Tensile strength (psi) | 14,300 | — |
| Tensile modulus (psi) | $1.43 \times 10^6$ | — |
| % Elongation | 1.26 | — |
| Flexural strength (psi) | 16,600 | 17,200 |
| Flexural modulus (psi) | $0.84 \times 10^6$ | $0.45 \times 10^6$ |
| Notched Izod (ft-lbs) | 4.5 | — |

A ⅛″ casting prepared from the same 50% solution of the solid VIC resin in styrene exhibits a heat deflection temperature of 255° F.

EXAMPLE 39

This example illustrates the preparation of an allophanate-free resin from a resin containing a large amount of allophanate.

A small reaction vessel is charged with 100 g. of a resin prepared according to Example 35, which by NMR analysis had an allophanate to urethane ratio of 0.45. 0.4 ml of Triton B (40% solution of benzyltrimethylammonium hydroxide in methanol) is added and 0.5 ml of a 10% solution of equal amounts of t-butylcatechol and the monomethyl ether of hydroquinone. The resulting mixture is heated for 1½ hours at 95° C. The final product is free of all detectable allophanate linkages upon NMR analysis.

EXAMPLE 40

A 500 ml, 3-necked flask equipped with mechanical stirrer, thermometer, air sparge, reflux condenser and dropping funnel is charged with 28.1 g. toluene diisocyanate (TDI) (80/20 mixture of 2,4- and 2,6-isomers) and 300 ml dry benzene. The mixture is heated to 55° C. and 21.3 grams of hydroxypropyl methacrylate is added over a 6-minute period. The reaction mixture is kept at 55° C. for an additional 16 minutes and then charged with 0.37 g. hydroquinone, 8.9 g. (0.07 moles) phenylisocyanate and 0.75 ml Triton B (40% solution of benzyltrimethylammonium hydroxide in methanol). Heating at 50° C. is continued for 45 minutes. A white precipitate is formed and is removed by filtration. The precipitate is identified as an isocyanurate containing both phenyl and tolyl groups by IR analysis.

EXAMPLE 41

A preferred method of preparing an allophanate-free isocyanurate composition of this invention is as follows: a 4-neck, round-bottom, 3-liter glass flask equipped with a thermometer, air and nitrogen inlet, dropping funnel and condenser is charged with 430 g. of hydroxypropyl methacrylate, 856 g. of styrene, 0.43 g. of cupric acetate monohydrate and 3.6 ml of a solution of t-butylcatechol in styrene. The solution is heated to 40° C. and 426 g. of toluene diisocyanate added over 45 minutes. The temperature of the reaction medium during the addition of the toluene diisocyanate is allowed to gradually rise. By a combination of the exothermic nature of the reaction and external heating the final temperature is 90° C. After the addition of the toluene diisocyanate, the temperature of the reaction mixture is kept at 90° C. for a further 15 minutes. The resulting dark green liquid is cooled to 70° C. and 2.8 ml of a 40% solution of benzyltrimethylammonium hydroxide dissolved in methanol is added in one lot. After the reaction mixture exotherms to 90° C., the temperature is held at 90° C. for 1 hour. Methanesulfonic acid (1.33 ml) is then added, the reaction mixture cooled and 4.4 ml of a 10% solution of t-butylcatechol in styrene added. The NMR spectrum of the product does not contain allophanate proton signals at about 10.6 ppm. This resin has a stability to 1% benzoyl peroxide of at least 7 hours at room temperature.

EXAMPLE 42

A 4-neck, round-bottom, 5-liter glass flask equipped with a thermometer, air and nitrogen inlet, dropping funnel and condenser is charged with 860 g. hydroxypropyl methacrylate, 1735 g. of styrene, 0.86 g. of cupric acetate monohydrate and 7.2 ml of a 10% solution of t-butylcatechol in styrene. The solution is heated to 41° C. and 876 g. of toluene diisocyanate added over 45 minutes. By a combination of the exothermic nature of the reaction and external heating, the temperature of the mixture is allowed to rise to 90° C. gradually during the 45 minutes. After the addition of the toluene diisocyanate, the temperature of the reaction mixture is kept at 90° C. for a further 15 minutes. The resulting dark green liquid is cooled to 67° C. (over 37 minutes) and 10 mls of a 40% solution of benzyltrimethylammonium hydroxide dissolved in methanol added in one lot. The mixture is heated over 5 minutes to 70° C. After a further 5 minutes an exotherm to 94° C. is observed. The exotherm is controlled by external cooling to 90° C. and the mixture then held at 90° C. for a further 131 minutes. 8.8 mls of a 10% solution of t-butylcatechol in styrene is added and the mixture cooled to 60° C. 1000 mls of the reaction mixture is retained and 1.9 mls of methanesulfonic acid added to the bulk of the reaction mixture. The NMR spectrum of this product does not contain any allophanate proton signal at 10.6 ppm. This product has a stability at room temperature to 1% benzoyl peroxide of at least 8 hours.

EXAMPLE 43

A 4-neck, round-bottom, 5-liter glass flask equipped with a thermometer, air and nitrogen inlet, dropping funnel and condenser is charged with 876 g. toluene diisocyanate, 1736 g. of styrene, 0.86 g. of cupric acetate monohydrate and 7.2 mls of a 10% solution of t-butylcatechol in styrene. The solution is heated to 40° C. and 860 g. of hydroxypropyl methacrylate added over 45 minutes. By a combination of the exothermic nature of the reaction and external heating, the temperature of the mixture is allowed to rise to 90° C. gradually during the 45 minutes. After the addition of the toluene diisocyanate, the temperature of the reaction mixture is kept at 90° C. for a further 15 minutes. The resulting dark green liquid is cooled to 72° C. over 30 minutes and 10 mls of a 40% solution of benzyltrimethylammonium hydroxide dissolved in methanol added in one lot. After 18 minutes at 71° C., an exotherm to 90.5° C. over 5 minutes is observed. The reaction mixture is held at 90° C. for 59 minutes and 2.66 mls of methanesulfonic acid added followed by 8.8 mls of a 10% solution of t-butylcatechol in styrene. The reaction mixture is then cooled to room temperature and stored. The NMR spectrum of this product does not contain an allophanate proton signal at 10.6 ppm. A ⅛ inch two-ply laminate of this resin containing 25% glass and cured with 1% benzoyl peroxide and 0.2% dimethylaniline at room temperature overnight followed by a 1-hour postcure at 100° C. has the following properties:

| Temperature | Flexural Strength, psi | Flexural Modulus, psi × 10⁶ |
|---|---|---|
| Room temperature | 14,100 | 0.79 |
| 300° F. | 13,600 | 0.32 |

EXAMPLE 44

A 4-neck, round-bottom, 5-liter glass flask, equipped with a thermometer, air and nitrogen inlet, 2 dropping funnels and condenser is charged with 1736 g. of styrene, 0.86 g. of cupric acetate monohydrate and 7.2 mls of a 10% solution of t-butylcatechol in styrene. The solution is heated to 41° C. and 860 g. of hydroxypropyl methacrylate and 876 g. of toluene diisocyanate added simultaneously over 44 minutes. By a combination of the exothermic nature of the reaction and external heating, the temperature of the mixture is raised gradually to 90° C. during the 45 minutes. After the addition, the temperature of the reaction mixture is kept at 90° C. for 15 minutes. The resulting liquid is cooled to 70° C. over 25 minutes and 10 mls of a 40% solution of benzyltrimethylammonium hydroxide dissolved in methanol added in one lot. After 15 minutes at 71° C. an exotherm to 90.5° C. over 4 minutes is observed. The reaction mixture is held at 90° C. for 59 minutes and 2.66 mls of methanesulfonic acid added followed by 8.8 mls of a 10% solution of t-butylcatechol in styrene. The reaction mixture is cooled to room temperature. The NMR spectrum of the product does not contain an allophanate proton signal at 10.6 ppm. A ⅛ inch two-ply laminate of this resin containing 25% glass and cured with 1% benzoyl peroxide and 0.2% dimethylaniline at room temperature overnight followed by a 1-hour postcure at 100° C. has the following properties:

| Temperature | Flexural Strength, psi | Flexural Modulus, psi × 10⁶ |
|---|---|---|
| Room temperature | 13,900 | 0.8 |
| 300° F. | 14,200 | 0.4 |

Although the process of this invention has been described with reference to specific reactions, conditions and reactants, it will be apparent that still other different and equivalent reactants and process conditions may be substituted for those specifically described, all within the sphere and scope of this invention.

EXAMPLE 45

A 3-liter, 4-necked flask equipped with a mechanical stirrer, thermometer, air sparge, reflux condenser and dropping funnel is charged with hydroxypropyl methacrylate (441 g, 2.94 moles), styrene (954.9 g, 9.15 moles) cupric acetate monohydrate (0.92 g) and 4 ml of a 10% solution of equal amounts of t-butyl catechol and the monomethyl ether of hydroquinone. The mixture is heated to 90° C. and toluene diisocyanate (TDI) (80/20 mixture of 2,4 and 2,6 isomers, 496.2 g, 2.85 moles) added over 30 minutes. The reaction mixture is held at 90° C. for 15 minutes and then cooled within 10 minutes to 65° C. Triton B (40% solution of benzyltrimethylammonium hydroxide in methanol, 5 ml) is then added and heat applied to raise the reaction temperature to 85° C. (10 minutes) and then raised to 95° C. for 35 minutes. The reaction mixture is stabilized with 2.5 ml of a 10% solution of equal amounts of t-butylcatechol and the monomethyl ether of hydroquinone. The trimerization reaction is terminated by the addition of methanesulfonic acid (1.5 ml). NMR analysis showed no detectable allophanate groupings.

EXAMPLE 46

A 3-liter, 4-necked flask equipped with a mechanical stirrer, thermometer, air sparge, reflux condenser and dropping funnel is charged with hydroxypropyl methacrylate (441 g, 2.94 moles), styrene (954.9 g, 9.15 moles), cupric acetate monohydrate (0.92 g) and 4 ml of a 10% solution of equal amounts of t-butylcatechol and the monomethyl ether of hydroquinone. The mixture is heated to 90° C. and toluene diisocyanate (TDI) (80/20 mixture of 2,4 and 2,6-ixomers, 522.3 g, 3.00 moles) added over a one hour period. The reaction mixture is kept at 90° C. for an additional hour and then cooled within 20 minutes to 55° C. Triton B (40% solution of benzyltrimethylammonium hydroxide in methanol, 5 ml) is then added and the exotherm controlled by use of a water bath. The reaction is permitted to exotherm to 65° C. As the reaction proceeds it will cool slowly and heat is only applied to keep it at 55° C. After two hours holding the isocyanate peak has completely disappeared in the IR. The trimerization reaction is terminated by the addition of methanesulfonic acid (15. ml) and stabilized by the addition of 5 ml of a 10% solution of equal amounts of t-butylcatechol and the monomethyl ether of hydroquinone. The product by NMR analysis shows an allophanate to urethane ratio of 0.1.

EXAMPLE 47

A chemical reactor equipped with agitator, condenser, gas pipe connections, vents, and port holes is first flushed with subsurface nitrogen. Subsequently an air sparge and nitrogen stream having relative flow rates of 1 to 3 are introduced into the reactor. 2.7 parts of hydroxypropyl methacrylate (HPMA) are then charged to the reactor. The air sparge and nitrogen streams are temporarily turned off and 0.0029 parts of copper acetate monohydrate and 0.012 parts of 20% solution of t-butylcatechol (TBC) in styrene are charged to the reactor under continuous agitation. The air sparge and nitrogen blanket streams are turned on again and 5.7 parts of styrene are charged to the reactor. The reaction mixture is then heated to about 40° C. When the temperature of the reaction mixture reaches 40° C. the incremental addition of an 80/20 mixture of 2,4- and 2,6-toluene diisocyanates (TDI) starts. An overall amount of 3.1 parts of TDI are charged over about one hour period. During this period the exotherm of the reaction of TDI with the alcohol raises the temperature of the reaction mixture to about 90° C. If at the end of the TDI addition the temperature is lower or higher than 90° external heating or cooling is applied respectively to bring the temperature to about 90° C. The reaction mixture remains at about 90° C. for at least one hour after the total amount of TDI has been added and until the NCO content of the reaction mixture drops to below 4.5% by weight. After both conditions are met the reaction mixture is cooled to about 50° C. 0.018 parts of 40% solution of benzyltrimethylammonium hydroxide in methanol (Triton B) (a trimerization catalyst), are then added to the reaction mixture. Soon after the addition of Triton B an exothermic reaction starts during the duration of which the temperature of the reaction mixture is maintained at 50° C. From the time the exotherm appears the viscosity and NCO content of the reaction mixture were monitored very closely. When the viscosity of the reaction mixture reaces 400-500 cps and the NCO level drops to below 0.2%, 0.007 parts of methanesulfonic acid are added to the reaction mixture and the mixture is then cooled. When the temperature reaches about 35° C., 0.014 parts of TBC are added and the reaction is then cooled to room temperature. The resulting vinyl isocyanurate is clear, has a light yellow brown color, a viscosity of about 400-500 cps and a shelf life longer than 3 months. NMR analysis of the product shows an allophanate to urethane ratio of 0.46. Laminates are prepared from this isocyanurate solution using a curing system of 0.2% dimethylaniline, 0.2% t-butylcatechol, and 2.0% benzoyl peroxide solution (50% active). ⅛″ two-ply laminates prepared from this resin retain more than 80% of their room temperature flexural and tensile strength at 300° F.

Having described the invention what is desired to be secured by Letters Patent is:

We claim:

1. A composition of matter comprising isocyanu rates of urethanes of an aromatic polyisocyanate and at least one vinylidene carbonyl oxy alkanol characterized by one of the following formulas:

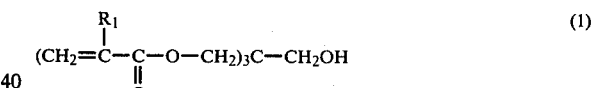

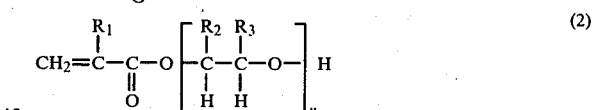

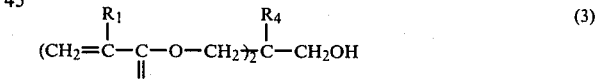

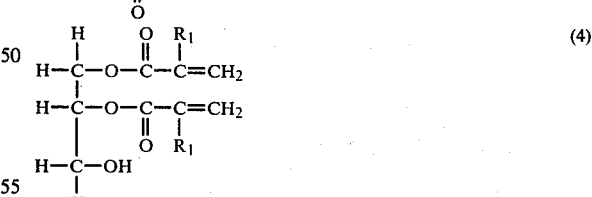

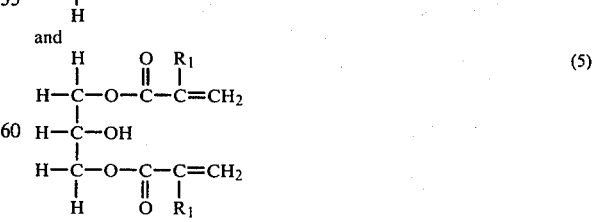

wherein $R_1$ is hydrogen or an alkyl group containing from one to four carbon atoms, $R_2$ is hydrogen, alkyl containing from 1 to 12 carbon atoms, or a chlorinated, brominated, or fluorinated alkyl group containing from 1 to 12 carbon atoms, $R_3$ is hydrogen, alkyl containing from 1 to 12 carbon atoms, or a chlorinated, brominated, or fluorinated alkyl group containing from 1 to 12 carbon atoms, $R_4$ is hydrogen, methyl or ethyl, and n is from one to four, with the proviso that $R_2$ and $R_3$ on adjacent carbon atoms are not both alkyl or chlorinated, brominated, or fluorinated alkyl.

2. A composition of claim 1 wherein the aromatic polyisocyanate is tolylene diisocyanate.

3. A composition of claim 1 wherein the aromatic polyisocyanate is polymethylene polyphenylene polyisocyanate.

4. A composition of claim 2 wherein the vinylidene carbonyl oxy alkanol is hydroxypropyl methacrylate, hydroxyethyl methacrylate, hydroxypropyl acrylate, hydroxyethyl acrylate, pentaerythritol triacrylate, pentaerythritol trimethacrylate, or a mixture thereof.

5. A composition of claim 2 wherein the vinylidene carbonyl oxy alkanol is hydroxypropyl methacrylate.

6. A composition of claim 2 wherein the vinylidene carbonyl oxy alkanol is hydroxyethyl methacrylate.

7. A composition of claim 2 wherein the vinylidene carbonyl oxy alkanol is hydroxypropyl acrylate.

8. A composition of claim 2 wherein the vinylidene carbonyl oxy alkanol is hydroxyethyl acrylate.

9. A composition of claim 2 wherein the vinylidene carbonyl oxy alkanol is pentaerythritol triacrylate.

10. A composition of claim 2 wherein the vinylidene carbonyl oxy alkanol is pentaerythritol trimethacrylate.

11. A composition of matter of claim 1 wherein the vinylidene carbonyl oxy alkanol is hydroxypropyl methacrylate, hydroxyethyl methacrylate, hydroxypropyl acrylate, hydroxyethyl acrylate, pentaerythritol triacrylate, pentaerythritol trimethacrylate, or a mixture thereof.

12. A composition of matter in accordance with claim 1 containing up to 49 mol percent of an isocyanurate of a monourethane of an aromatic polyisocyanate and a monohydric phenol or a monohydric alcohol which is not a said vinylidene carbonyl oxy alkanol.

13. A composition of matter in accordance with claim 1 containing up to 33 mol percent of an isocyanurate of monourethanes of aromatic polyisocyanates and a dihydric alcohol or dihydric phenol.

14. A solution of an isocyanurate composition of claim 1 dissolved in a free-radical polymerizable ethylenically unsaturated solvent.

15. A solution of claim 14 wherein the solvent is selected from the group consisting of divinylbenzene, styrene, methyl acrylate, methyl methacrylate, ethyl acrylate, ethyl methacrylate, 2-ethylhexyl acrylate, 2-ethylhexyl methacrylate, butyl acrylate, butyl methacrylate, cyclohexyl acrylate, cyclohexyl methacrylate, acrylic acid, methacrylic acid, hydroxyethyl acrylate, hydroxyethyl methacrylate, hydroxypropyl acrylate, hydroxypropyl methacrylate, 2,3-dibromopropyl acrylate, 2,3-dibromopropyl methacrylate, tetramethylene glycol diacrylate, trimethylol propane triacrylate, pentaerythritol triacrylate, neopentyl glycol diacrylate, 1,3-butyleneglycol diacrylate, chlorostyrene, acrylonitrile, vinylidene chloride, vinyl acetate, vinyl stearate, vinyltolylene, hexanediol diacrylate, hexanediol dimethacrylate, and mixtures thereof.

16. A polymer obtained by polymerizing an ethylenically unsaturated isocyanurate composition of claim 1.

17. A polymer prepared by copolymerizing an ethylenically unsaturated isocyanurate composition of claim 1 with an ethylenically unsaturated copolymerizable compound.

18. A polymer prepared by polymerizng the solution of claim 14.

19. A composition of claim 12 wherein the monohydric alcohol is a brominated monohydric alcohol.

20. A composition of claim 12 wherein the monohydric alcohol is 2,3-dibromo-1-propanol.

21. A solution of claim 14 wherein the solvent is styrene or a mixture of styrene and methyl methacrylate.

22. A solution of claim 14 containing from 50% to 95% by weight of solvent and from 50% to 5% by weight of dissolved unsaturated isocyanurate and having a Brookfield viscosity of at least 100 centipoise at 25° C. as measured on a Brookfield Model LVT Viscometer using a number two spindle and 30 rpm.

23. A composition of claim 1 comprising a mixture of isocyanurates containing only one isocyanurate ring and isocyanurates containing more than one isocyanurate ring.

24. A polymer of claim 17 prepared by copolymerizing from about 80% to about 30% by weight of styrene with from about 20% to about 70% by weight of an isocyanurate of a urethane of tolylene diisocyanate and hydroxypropyl methacrylate.

25. A composition of claim 1 wherein the isocyanurates are polyisocyanurates.

26. A composition of claim 1 which exhibits infrared peaks at 5.75-6 microns, 6.1-6.35 microns, 6.9-7.2 microns, and 10.15-10.85 microns.

27. A composition of claim 26 which exhibits infrared peaks at 5.8-5.9 microns, 6.2-6.3 microns, 7.00-7.15 microns, and 10.2-10.75 microns.

28. A composition of claim 5 dissolved in styrene which exhibits infrared peaks at 5.85 microns, 6.23 microns, 7.1 microns, and 10.6 microns.

29. A solution of an isocyanurate composition of claim 5 dissolved in styrene and which exhibits NMR signals at 9.6±0.2, 8.8±0.2, 7.50, 7.48, 7.44, 7.41, 7.36, 7.33, 7.29, 7.26, 6.79, 6.71, 6.57, 5.93, 5.91, 5.70, 5.69, 5.33, 5.31, and 5.19 and which exhibits infrared peaks at 5.85 microns, 6.23 microns, 7.1 microns, and 10.6 microns.

30. A solution of claim 26 which exhibits an NMR signal at 10.6±0.2.

31. A composition of claim 1 which has a stoichiometric ratio of allophanate groups to urethane groups of not more than about 0.7.

32. A composition of claim 1 which has a stoichiometric ratio of allophanate groups to urethane groups of not more than about 0.2.

33. A laminate composition comprising at least 20% by weight of the composition of claim 1 and not more than 80% by weight of a wettable fiber and cured with a free radical initiator.

34. A composition of claim 1 containing up to 65% by weight of a urethane having the formula $(R_a)$ $(R_b)k$ where $R_a$ is an aromatic radical free of a group which is reactive with an isocyanate group and is obtained by removing the isocyanate groups from an aromatic polyisocyanate, k is an integer which is equal to the number of isocyanate groups present in the polyisocyanate, and $R_b$ is

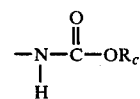

where $R_c$ is a monovalent organic radical having the formula obtained by removing a hydroxyl group from a vinylidene carbonyl oxy alkanol characterized by formula (1) thru (5) recited in claim 1.

* * * * *

UNITED STATES PATENT AND TRADEMARK OFFICE
CERTIFICATE OF CORRECTION

PATENT NO. : 4,195,146
DATED : March 25, 1980
INVENTOR(S) : Kenneth H. Markiewitz; Alfred J. Restaino It is certified that error appears in the above-identified patent and that said Letters Patent are hereby corrected as shown below:

Column 3, line 14, "yethgyl" should read -- yethyl --.

Column 4, approximately line 62, between structures, insert -- or --.

Column 16, line 39, "5/8" should read -- 1/8 --.

Column 16, line 40, "5/8" should read -- 1/8 --.

Column 23, line 62, delete "," after "methanol)".

Column 28, line 32, "isocyanu rates" should read -- isocyanurates --.

Signed and Sealed this

Ninth Day of September 1980

[SEAL]

Attest:

SIDNEY A. DIAMOND

Attesting Officer

Commissioner of Patents and Trademarks